US008460264B2

United States Patent
Otsubo (10) Patent No.: US 8,460,264 B2
(45) Date of Patent: Jun. 11, 2013

(54) WEARING ARTICLE AND METHOD FOR MAKING THE SAME

(75) Inventor: Toshifumi Otsubo, Kagawa (JP)

(73) Assignee: Uni-Charm Corporation, Ehime (JP)

(*) Notice: Subject to any disclaimer, the term of this patent is extended or adjusted under 35 U.S.C. 154(b) by 21 days.

(21) Appl. No.: 12/919,590

(22) PCT Filed: Dec. 16, 2008

(86) PCT No.: PCT/JP2008/072821
§ 371 (c)(1),
(2), (4) Date: Nov. 11, 2010

(87) PCT Pub. No.: WO2009/110153
PCT Pub. Date: Sep. 11, 2009

(65) Prior Publication Data
US 2011/0046598 A1    Feb. 24, 2011

(30) Foreign Application Priority Data
Mar. 3, 2008    (JP) ................................. 2008-052510

(51) Int. Cl.
*A61F 13/15*    (2006.01)
(52) U.S. Cl.
USPC .............................. 604/385.22; 604/385.01
(58) Field of Classification Search
USPC ............. 604/385.27, 385.19, 385.24, 385.01, 604/395, 385.22, 385.29
See application file for complete search history.

(56) References Cited

U.S. PATENT DOCUMENTS 6,716,205 B2* 4/2004 Popp et al. ............... 604/385.24
7,314,465 B2* 1/2008 Van Gompel et al. ........ 604/395
7,824,389 B2* 11/2010 Veith ........................ 604/385.23
2005/0055005 A1* 3/2005 Cazzato et al. .......... 604/385.27
2010/0069872 A1* 3/2010 Lindstrom ............... 604/385.22

FOREIGN PATENT DOCUMENTS

| JP | 2001000478 | 1/2001 |
| JP | 2003024379 | 1/2003 |
| JP | 2003305080 | 10/2003 |
| JP | 2006130053 | 5/2006 |
| JP | 2007077531 | 3/2007 |

OTHER PUBLICATIONS

International Search Report for PCT/JP2008/072821 issued Mar. 17, 2009.

* cited by examiner

*Primary Examiner* — Lynne Anderson
*Assistant Examiner* — Bradley Philips
(74) *Attorney, Agent, or Firm* — Lowe Hauptman Ham & Berner, LLP (57) ABSTRACT

The present invention aims to provide an improved wearing article allowing the dimension of the leg-openings to be adequately large without causing leakage of urine. A chassis is formed in a crotch region with an opening extending through inner and outer sheets in the thickness direction. The opening extends across the crotch region in a longitudinal direction partially into front and rear waist regions and also extends through parts of respective waist region elastic sheets in the thickness direction. An absorbent panel functioning as a liquid-absorbent structure is attached to the skin-facing surface of the chassis to cover the opening. The liquid-absorbent panel is joined along both side edges thereof to the inner sheet and the waist region elastic sheets by bonding or sealing technique and along front and rear ends thereof to the waist region elastic sheets by bonding or sealing technique.

8 Claims, 7 Drawing Sheets

WEARING ARTICLE AND METHOD FOR MAKING THE SAME

RELATED APPLICATIONS

The present application is a national phase of PCT/JP2008/072821, filed Dec. 16, 2008, and claims priority from, Japanese Application Number 2008-052510, filed Mar. 3, 2008.

TECHNICAL FIELD

The present invention relates to wearing articles and methods for making the same and more particularly to absorbent wearing articles such as disposable diapers, toilet-training pants and incontinent briefs and methods for making the same.

RELATED ART

It is known, for example, from JP 2001-478 A (PATENT DOCUMENT 1) to attach elastic members to front and rear waist regions in a disposable diaper. According to the disclosure of this PATENT DOCUMENT, the diaper basically comprises a chassis having a front waist region, a rear waist region, a crotch region, a skin-facing side and a garment-facing side, and an absorbent structure attached to the inner surface of the chassis facing the wearer's body. The chassis is provided in the front and rear waist regions thereof with waist region elastic members extending in a transverse direction attached under tension thereto, respectively, so that the absorbent structure overlaps these waist region elastic members.

According to the disclosure of PATENT DOCUMENT 1, a method for making such diaper comprises steps of: attaching absorbent structures arranged at regular intervals to a web of nonwoven fabric sheet defining chassis; cutting out the web of nonwoven fabric sheet defining chassis between each pair of the adjacent absorbent structures and folding the web of chassis defining sheet along an imaginary longitudinal center line in two; and cutting off the web of nonwoven fabric sheet defining chassis between each pair of the adjacent absorbent structures, more specifically, along an imaginary transverse center line of the cut out portion of the web of nonwoven fabric sheet defining chassis to form opposite side edges which are then bonded to each other to form a waist-opening and a pair of leg-openings for each diaper.
PATENT DOCUMENT 1: JP 2001-478 A

DISCLOSURE OF THE INVENTION

Problem to be Solved by the Invention

In the disposable diaper as has been described above, the leg-openings may be dimensioned larger to make it easy to guide the wearer's legs therethrough and to put the diaper on the wearer's body. To dimension larger the leg-openings, it is necessary to dimension larger in the longitudinal direction of the cut-out area of the web of sheet defining chassis. To enlarge the dimension of the cut-out area, it may be contemplated to enlarge the interval between each pair of the adjacent absorbent structures. However, such measure will increase the quantity of the nonwoven fabric sheet per diaper and may correspondingly increase a manufacturing cost. In addition, the enlarged interval between each pair of the adjacent absorbent structures will correspondingly enlarge the waist-opening and, to ensure that the waist-opening properly fits to the wearer's waist under contraction of the associated elastic members, the number of gathers created due to contraction of the elastic members will be unacceptably increased. Increased gathers will unacceptably increase gaps between the diaper and the wearer's body and will cause leakage of bodily fluids such as urine and leave compression traces on the wearer's skin.

To obtain the leg-openings of sufficiently large dimension without unacceptably enlarging the dimension of the waist-opening, the width dimension of the crotch region between a pair of leg-openings will be inevitably reduced and correspondingly the width dimension of the absorbent structure will be reduced. The excessively reduced width dimension of the absorbent structure will necessarily reduce the absorption capacity for urine and will cause leakage of urine.

In view of the problem as has been described above, it is a principal object of the present invention to provide an improved wearing article allowing the dimension of the leg-openings to be adequately large without causing leakage of urine.

Measure to Solve the Problem

The object set forth above is achieved, according to the present invention on a first aspect thereof, by an improvement in the wearing article comprising a chassis having a longitudinal direction, a transverse direction, a skin-facing inner surface, a garment-facing outer surface, a front waist region, a rear waist region and a crotch region extending between the front and rear waist regions, these regions being contiguous one with another, a liquid-absorbent structure lying at least in the crotch region, and waist region elastics attached under tension in the transverse direction to the front and rear waist regions, respectively, wherein the chassis is contoured by front and rear ends opposed to each other in the longitudinal direction and extending in the transverse direction and side edges opposed to each other in the transverse direction and extending in the longitudinal direction so that the front and rear ends of the front and rear ends cooperate with each other to form a waist-opening and the side edges cooperate with each other to form a pair of leg-openings in the crotch region.

The improvement according to the present invention on the first aspect thereof is characterized in that the chassis includes an opening formed to extend from at least any one of the front and rear waist regions across the crotch region and the liquid-absorbent structure is attached to the chassis to cover the opening; and the waist region elastics are attached to the front and rear waist regions outboard of the opening as viewed in the transverse direction and the opening takes its desired shape under contraction of the waist region elastics in the transverse direction.

According to one preferred embodiment of the present invention on the first aspect thereof, the side edges of the chassis comprise front and rear waist regions' side edges lying in the front and rear waist regions and crotch region's side edges lying in the crotch region; and leg elastics are attached under tension to the chassis along the crotch region's side edges and at least parts of the respective leg elastics lie outboard of the opening as viewed in the transverse direction.

According to another preferred embodiment of the present invention on the first aspect thereof, the waist region elastics are formed of stretchable and contractible waist region elastic sheets attached to the skin-facing inner surface of the chassis.

The object set forth above is achieved, according to the present invention on a second aspect thereof, by an improvement in the method for making the above-described wearing article, comprising steps of: attaching the waist region elastics under tension in a conveying direction to a web of sheet defining the chassis being conveyed by a conveying structure;

forming the web of sheet defining the chassis and the waist region elastics attached thereto with the openings; attaching the liquid-absorbent structures to the web of sheet defining the chassis to cover the openings; and cutting off the web of sheet defining the chassis outside and along the side edges of the liquid-absorbent structure extending orthogonally to the conveying direction.

According to one preferred embodiment of the present invention on the second aspect thereof, the method further includes a step of cutting off a web of liquid-absorbent sheet to form the liquid-absorbent structure and a step of rotating the liquid-absorbent structure by an angle of about 90° relative to the conveying direction.

According to another preferred embodiment of the present invention on the second aspect thereof, the opening is formed by making a cut in or cutting off the web of sheet defining the chassis.

Effect of the Invention

The chassis includes an opening formed to extend from at least any one of the front and rear waist regions across the crotch region and the liquid-absorbent structure is attached to the chassis to cover the opening. The opening takes its desired shape under contraction of the waist region elastics and therefore the transverse dimension of the opening in the waist regions as well as in the crotch region can be generally increased. Specifically, even if the cut-out in the crotch region to form the leg-openings is relatively deep, it will be unnecessary to reduce the width dimension of the liquid-absorbent structure and leakage of bodily fluids such as urine will be reliably restricted. The leg-openings can be safely enlarged and thereby the wearing article can be smoothly put on the wearer's body.

The waist region elastics are provided outboard of the opening as viewed in the transverse direction so that no contractile force of the waist region elastics is exerted on the liquid-absorbent structure even when the opening is covered with the liquid-absorbent structure. As a consequence, contraction of the waist region elastics would not cause the liquid-absorbent structure to get wrinkled.

The leg elastics are attached under tension to the chassis along the crotch region's side edges and outboard of the opening as viewed in the transverse direction. With such arrangement, the opening can be sufficiently broadened and the liquid-absorbent structure would not get wrinkled due to the leg elastics.

The waist region elastics formed of stretchable and contractible waist region elastic sheets allow the elasticity of these elastics to be exerted on the opening and irregularities along the periphery of the opening to be alleviated.

The method for making the above-described wearing article, comprising steps of: attaching the waist region elastics under tension in the conveying direction to the web of sheet defining the being conveyed by the conveying structure; forming the web of sheet defining the chassis and the waist region elastics attached thereto with the opening; attaching the liquid-absorbent structure to the chassis to cover the opening; and cutting off the web of sheet defining the chassis outside and along the side edges of the liquid-absorbent structure extending orthogonally to the conveying direction. In this way, the wearing articles each formed with the opening can be made in a series of steps.

The method further includes a step of cutting off web of liquid-absorbent sheet to form the liquid-absorbent structure and a step of rotating the liquid-absorbent structure by an angle of about 90° relative to the conveying direction. In this way, the liquid-absorbent structures also can be attached to the chassis in a series of steps.

When the opening is formed by making a cut in the web of sheet defining the chassis, formation of the opening is efficiently simplified. When the opening is formed by cut-out of the web, the width dimension of the opening can be larger than in the case of cut in the web.

IDENTIFICATION OF REFERENCE NUMERALS USED IN THE DRAWINGS 1 diaper
2 chassis
3 liquid-absorbent structure
4 front waist region
5 rear waist region
6 crotch region
14 waist region elastic sheet (waist region elastics
15 opening
16 liquid-absorbent panel (liquid-absorbent structure)
29 leg elastics' front halves
30 leg elastics' rear halves
31 web of sheet defining chassis
42 web of liquid-absorbent sheet

DETAILED DESCRIPTION OF THE PREFERRED EMBODIMENTS

Details of the embodiments according to the present invention will be more fully understood from the description of a disposable diaper as a typical embodiment of the present invention, given hereunder with reference to the accompanying drawings.

Figure 1:
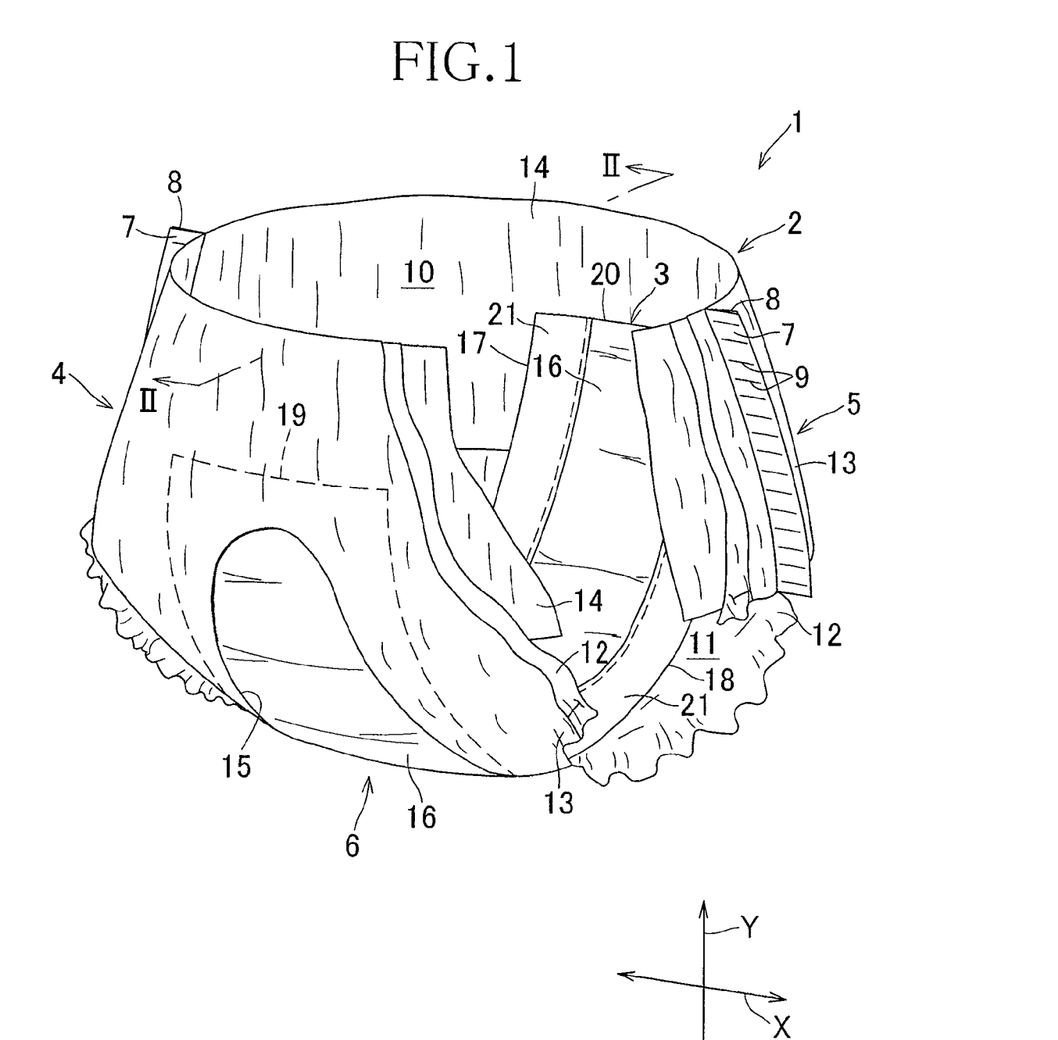
FIG. 1 is a perspective view of a diaper.

FIG. 1 is a perspective view showing a diaper 1 put on the wearer's body as partially cutaway for convenience of illustration. As will be apparent from FIG. 1, the diaper 1 basically comprises a chassis 2 and a liquid-absorbent structure 3. The chassis 2 is pants-shaped and comprises a front waist region 4, a rear waist region 5 and a crotch region 6 extending between the front and rear waist regions 4, 5. A direction extending from the front waist region 4 across the crotch region 6 to the rear waist region 5 is designated herein as a longitudinal direction Y and a direction extending orthogonally to this longitudinal direction Y is designated herein as a transverse direction X.

Respective side edges 7, 7 of the front waist region 4 are put flat and bonded together with respective side edges 8, 8 of the rear waist region 5 at a plurality of joints 9 arranged intermittently along the respective side edges 7, 8 to form seams. Thereupon, a region surrounded by the front and rear waist regions 4, 5 is formed with a waist-opening 10 and regions surrounded by the seams 9 and the crotch region 6 are formed with a pair of leg-openings 11, respectively.

The chassis 2 includes an inner sheet 12 defining a skin-facing inner surface, an outer sheet 13 defining a garment-facing outer surface and waist region elastic sheets 14 lying on the skin-facing side of the inner sheet 12. Stock material which may be used for the inner and outer sheets 12, 13 includes, for example, an air-permeable nonwoven fabric. As the stock material for the waist region elastic sheets 14, a liquid-pervious elastic nonwoven fabric respectively extending between each pair of the side edges 7, 7 and between each pair of the side edges 8, 8 may be used. The waist region elastic sheets 14 made of such liquid-pervious elastic nonwoven fabric are bonded under tension in the transverse direction X to the inner sheet 12 in the front and rear waist regions 4, 5, respectively, by heat or ultrasonic sealing or adhesive bonding.

The chassis 2 is formed in the crotch region 6 thereof with an opening 15 extending through the inner and outer sheets 12, 13 in the thickness direction thereof. The opening 15 extends across the crotch region 6 in the longitudinal direction Y partially into the front and rear waist regions 4, 5 and extends through parts of the respective waist region elastic sheets 14 also in the thickness direction. The chassis 2 includes a liquid-absorbent panel 16 as the liquid-absorbent structure 3 attached to its skin-facing inner surface to cover the opening 15. The liquid-absorbent panel 16 is contoured by side edges 17, 18 opposed to each other in the transverse direction X and extending in the longitudinal direction Y and front and rear ends 19, 20 opposed to each other in the longitudinal direction and extending in the transverse direction X. The liquid-absorbent panel 16 has the side edges 17, 18 bonded to the inner sheet 12 and the waist region elastic sheets 14 by adhesive bonding or heat or ultrasonic sealing and the front and rear ends 19, 20 bonded to the waist region elastic sheets 14 by adhesive bonding or heat or ultrasonic sealing. The liquid-absorbent panel 16 is provided along the side edges 17, 18 thereof with leak-barrier cuffs 21, 21, respectively.

Figure 2:
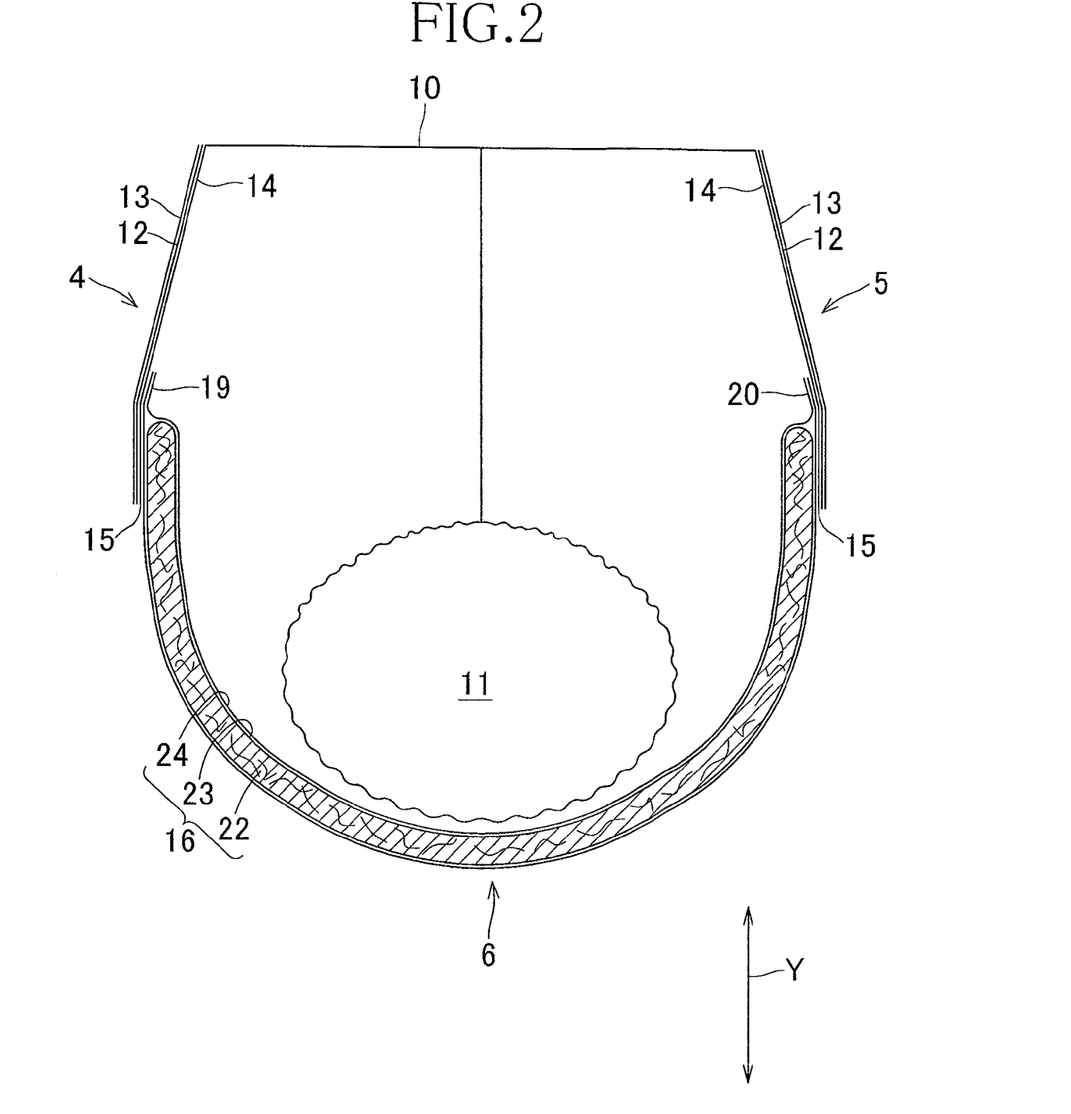
FIG. 2 is a sectional view taken along the line II-II in FIG. 1.

FIG. 2 is a sectional view taken along the line II-II in FIG. 1. As will be apparent from FIG. 2, the liquid-absorbent panel 16 is bonded to the skin-facing inner surface of the waist region elastic sheets 14 so as to cover the opening 15 of the chassis 2. The liquid-absorbent panel 16 comprises a liquid-absorbent core 22, a liquid-absorbent/dispersant sheet 23 such as a tissue paper with which the liquid-absorbent core 22 is wrapped and a surfacing sheet adapted to cover the liquid-absorbent/dispersant sheet 23. While the present embodiment uses such liquid-absorbent panel 16 as the liquid-absorbent structure 3, it should be understood that the present invention is not limited to this but the commonly used liquid-absorbent panel 16 may be used.

Figure 3:
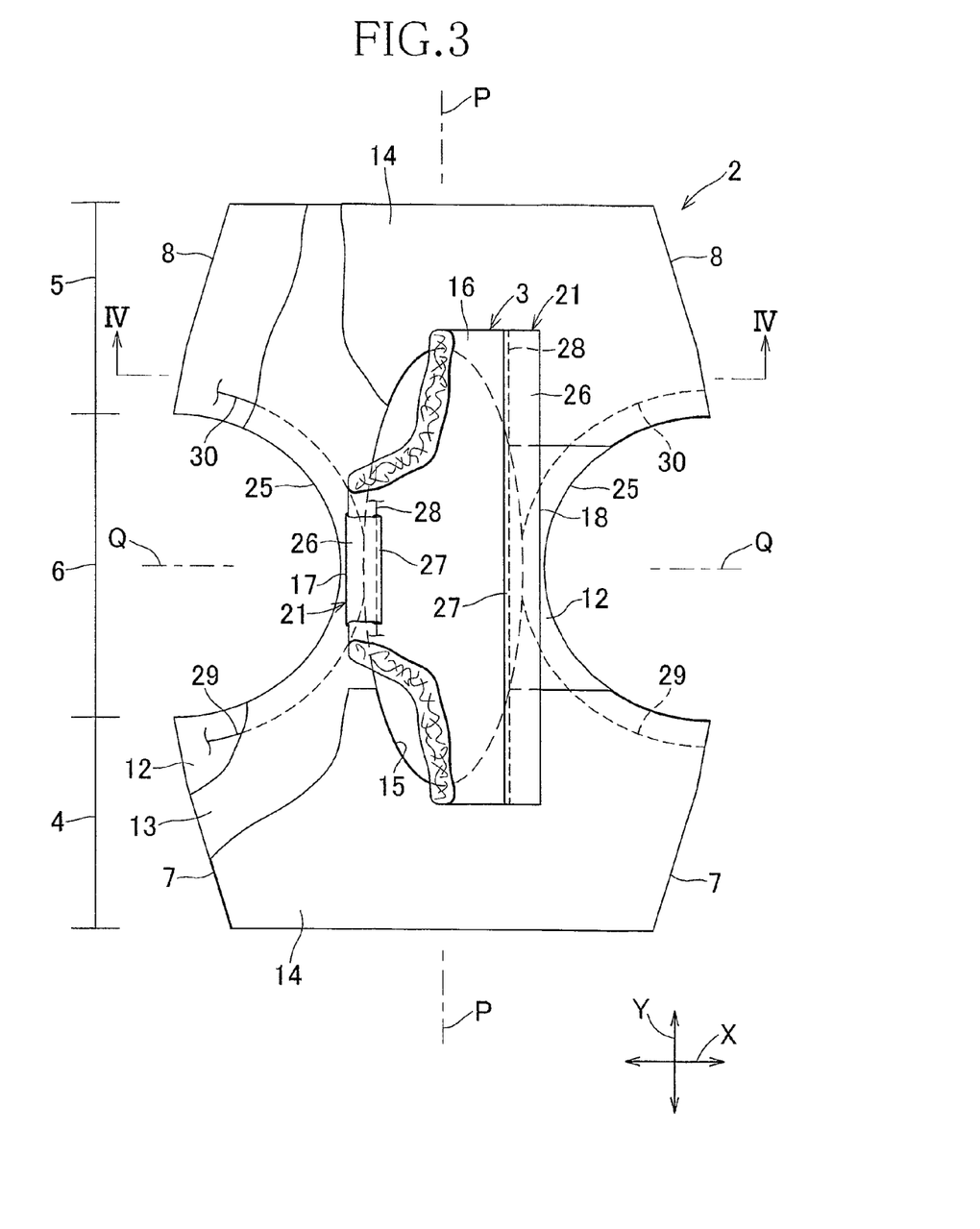
FIG. 3 is a plan view showing the diaper of FIG. 1 as has been flatly developed.
Figure 4:
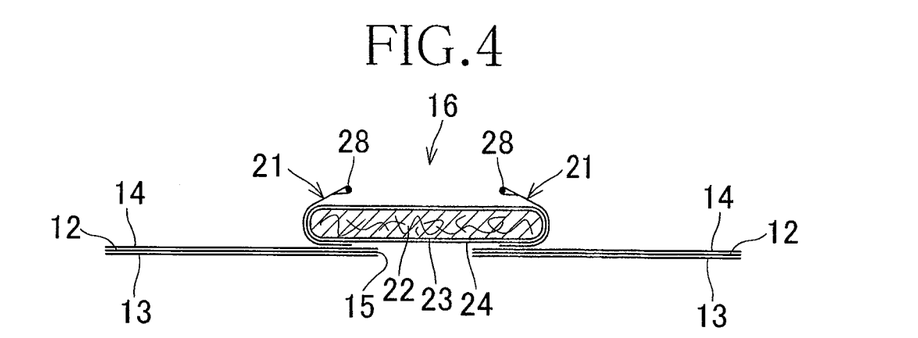
FIG. 4 is a sectional view taken along the line IV-IV in FIG. 3.

FIG. 3 is a plan view of the diaper 1 having the front and rear waist regions peeled off from each other at the joints 9 and developed in the longitudinal direction Y as well as in the transverse direction X so that the front waist region 4, the rear waist region 5 and the crotch region 6 may lie in the same plane. It should be appreciated that FIG. 3 is partially cutaway for convenience of illustration. The diaper 1 has the longitudinal center line P-P bisecting a dimension of the diaper 1 in the transverse direction X and the transverse center line Q-Q bisecting a dimension of the diaper 1 in the longitudinal direction Y wherein the diaper 1 is laterally symmetric about the longitudinal center line P-P. FIG. 4 is a sectional view taken along the line IV-IV in FIG. 3.

Referring to FIG. 3, the chassis 2 includes leg side edges 25 defined between the waist regions' side edges 7, 8 to extend across the crotch region 6 in the longitudinal direction Y. The chassis 2 is trimmed along the leg side edges 25 to be convex toward the longitudinal center line P-P. In other words, the chassis 2 is shaped to have its length dimension in the transverse direction X smaller in the vicinity of the transverse center line Q-Q than the length dimension in the remaining region. Consequently, the chassis 2 as a whole has concave shape curved inwardly.

The chassis 2 is provided on its skin-facing inner surface with the liquid-absorbent panel 16 bonded thereto. This liquid-absorbent panel 16 is shaped in a rectangle and bonded to the inner sheet 12 to cover the opening 16. The opening 15 partially extends into the front and rear waist regions 4, 5, in other words, the respective waist region elastic sheets 14 also are formed with associated partial sections of the opening 15 and necessarily the liquid-absorbent panel 16 is bonded to the respective waist region elastic sheets 14 in the front and rear waist regions 4, 5.

The liquid-absorbent panel 16 is provided with leak-barrier cuffs 21 formed of a pair of sheets extending in the longitudinal direction Y symmetrically about the longitudinal center line P-P. These sheets may be formed of, for example, a nonwoven fabric or plastic film which is preferably of liquid-impervious nature.

The leak-barrier cuffs 21 are provided on the skin-facing inner surface of the liquid-absorbent panel 16 and include fixed edges permanently bonded to the liquid-absorbent panel 16 along outer side edges 26 overlapping the side edges 17, 18 of the liquid-absorbent panel 16, respectively, and free edges adapted to be spaced upward from the liquid-absorbent panel 16 along inner side edges 27 opposed to the outer side edges 26. Cuff elastics 28 extending in the longitudinal direction Y are attached along the respective inner side edges 27 under tension to the respective leak-barrier cuffs 21 so that the free edges may be spaced upward from the liquid-absorbent panel 16 under contractile force of the cuff elastics 28.

Outboard of the respective side edges 17, 18 of the liquid-absorbent panel 1 as viewed in the transverse direction X, leg elastics' front and rear halves 29, 30 formed by, for example, rubber thread or rubber ribbon are attached to the chassis 2. The leg elastics' front halves 29 extend into the front waist region 4 and the leg elastics' rear halves 30 extend into the rear waist region 5. The leg elastics' front and rear halves 29, 30 respectively curve along the leg side edges 25 and are attached under tension to the chassis 2. The leg elastics' front and rear halves 29, 30 are interrupted by the opening 15 and therefore not continuous in the transverse direction X.

Figure 5:
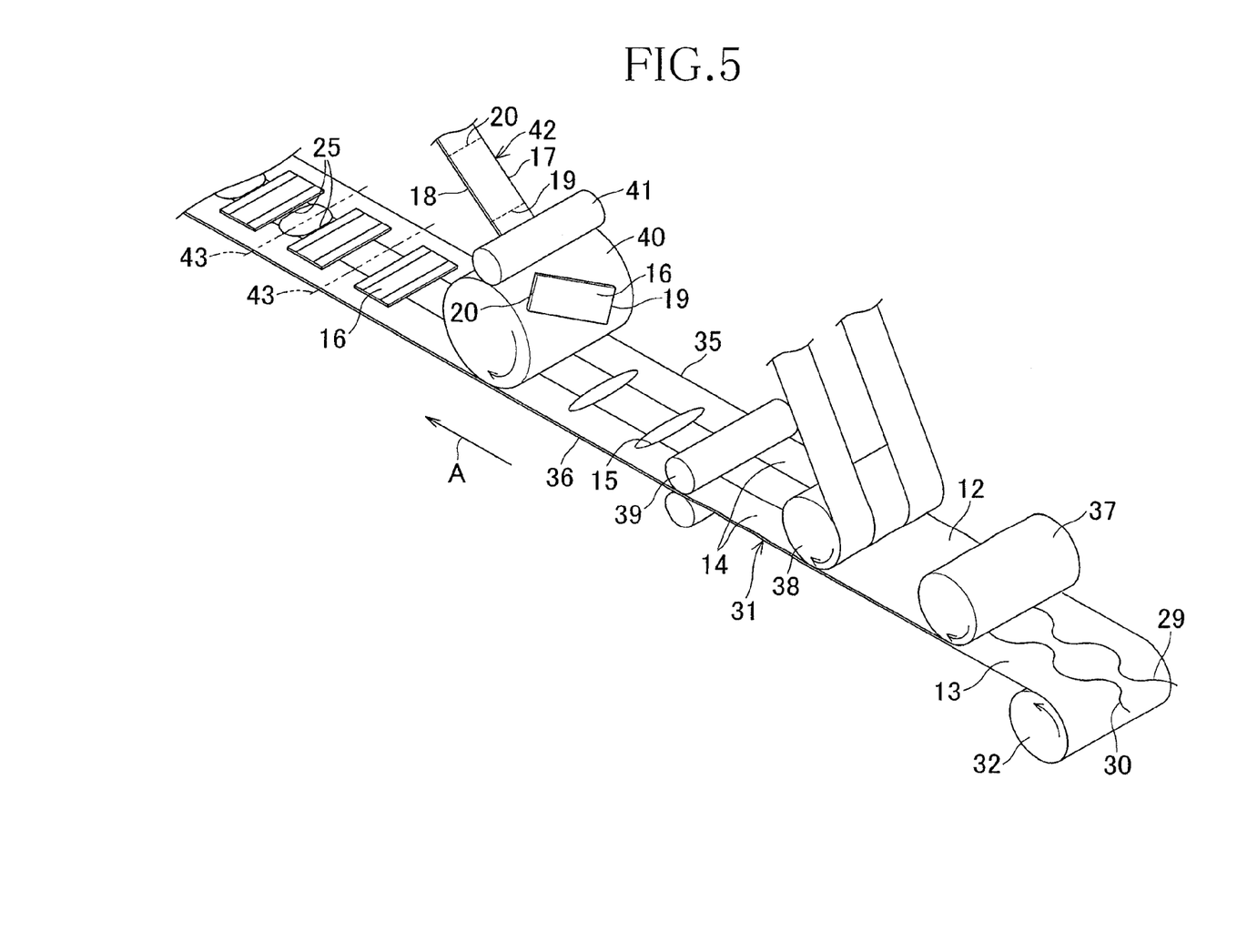
FIG. 5 is a schematic diagram illustrating a process for making the diaper.

The diaper 1 as has been described above is obtained by successively following steps of the process as schematically illustrated by FIG. 5. In a first step, a web of the outer sheet 13 is conveyed by a first roller 32 in a conveying direction indicated by the arrow A. The leg elastics' front and rear halves 29, 30 are fed onto the web of outer sheet 13 and continuously attached thereto under tension.

Figure 6:
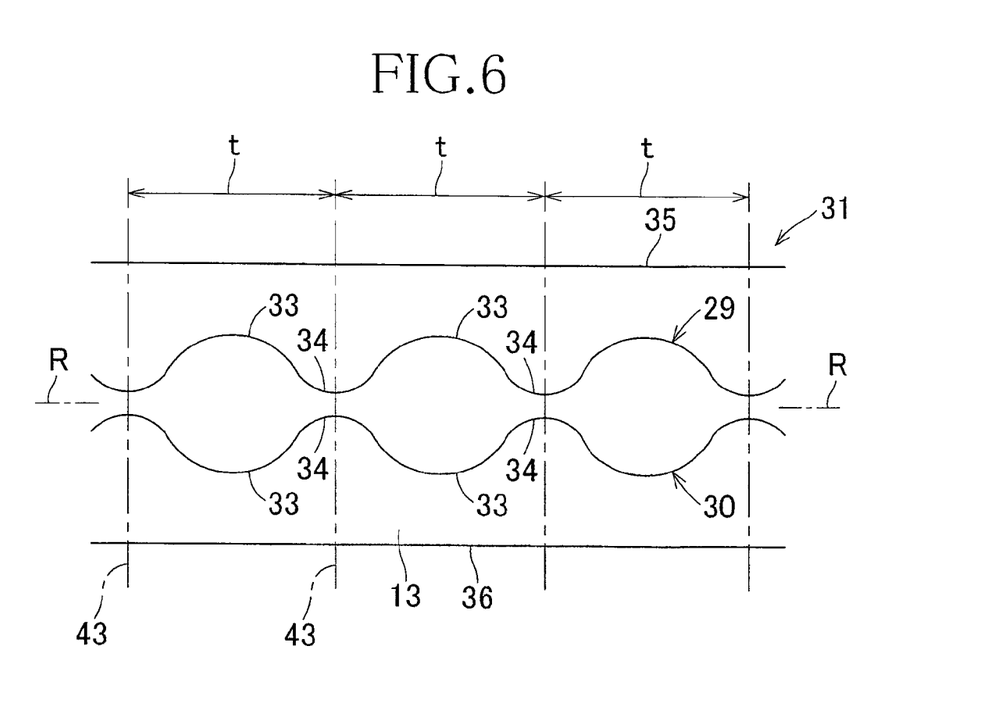
FIG. 6 is an explanatory diagram of the process for making the diaper.

FIG. 6 illustrates a fashion in which the leg elastics' front and rear halves 29, 30 are attached to the web of the outer sheet 13. As will be apparent from FIG. 6, the leg elastics' front and rear halves 29, 30 comprise distance increasing segments 33 along which the leg elastics' front and rear halves 29, 30 are being spaced from each other and distance reducing segments 34 along which the elastics' front and rear halves 29, are coming close to each other wherein these segments 33, 34 alternate in contiguous fashion. More specifically, the leg elastics' front and rear halves 29, 30 curve from respective points on the distance increasing segments 33 which are closest to upper and lower ends 35, 36 of the web of the outer sheet 13 toward the center line R-R bisecting a distance between the upper and lower ends 35, 36, then trace linear curves generally in parallel to the center line R-R and, along the adjacent distance reducing segment 34, the leg elastics' front and rear halves 29, 30 curve again toward the upper and lower ends 35, 36. Assumed that respective segments extending in the conveying direction from the points which are closest to the upper and lower ends 35, 36, respectively, to the adjacent points which are closest to the upper and lower ends 35, 36 are designated as one cycle t, one individual diaper 1 can be obtained per one cycle t.

In a second step, as will be apparent from FIG. 5, a web of the inner sheet 12 is fed in the direction of the arrow A by a second roller 37. The web of the inner sheet 12 fed in this manner is bonded or sealed to the web of the outer sheet 13 via the leg elastics' front and rear halves 29, 30 to form a web of the chassis defining sheet 31.

In a third step, the leg elastics' front and rear halves 29, 30 are attached to the web of sheet defining the chassis 31. Specifically, a pair of the webs of the waist region elastic sheets 14 are fed by a third roller 38 in the direction of the arrow A toward the web of the inner sheet 12 constituting the web of sheet defining the chassis 31 and attached to the surface of the web of the inner sheet 12 facing away from the web of the outer sheet 13. The webs of the waist region elastic sheets 14 are attached under tension in the conveying direction to the web of the inner sheet 12 to be deviated away from the center line R-R toward the upper and lower ends 35, 36, respectively. In other words, none of the webs of the waist region elastic sheets 14 is present in the vicinity of the center line R-R.

Figure 7:
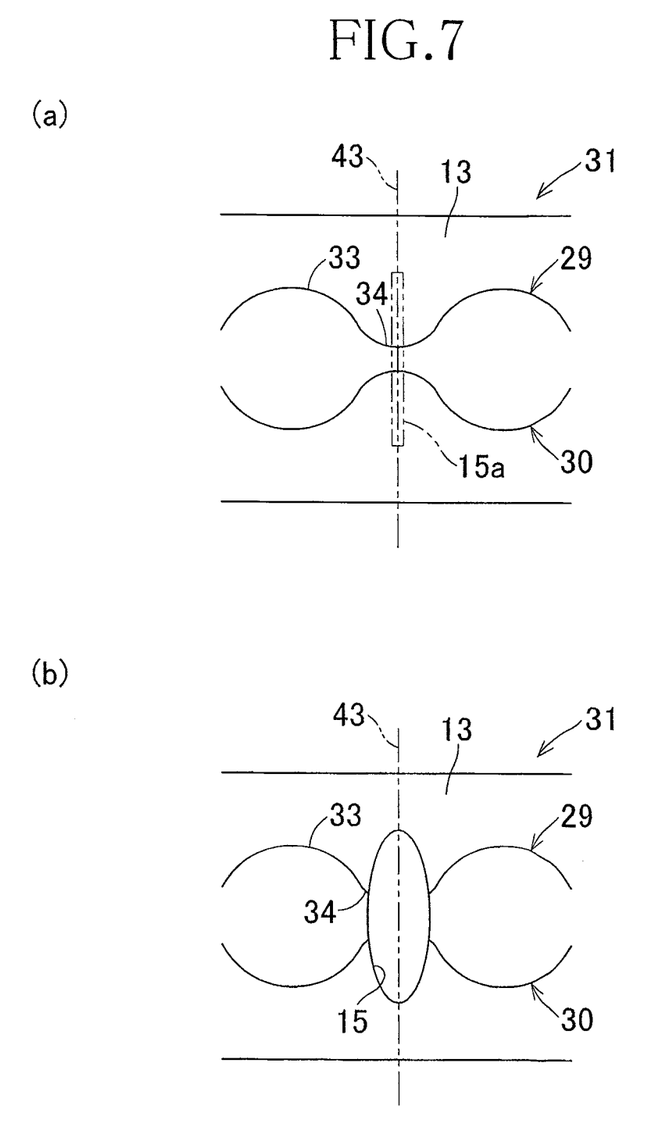
FIG. 7 is an explanatory diagram of the process for making the diaper.

In a fourth step, the web of sheet defining the chassis 31 is formed with the openings 15 by a cutter 39 provided ahead of the third roller 38 as viewed in the conveying direction. The cutter 39 cuts the web of the chassis defining sheet 31 through the thickness direction thereof at regular intervals. FIG. 7 schematically illustrates the web of sheet defining the chassis 31 before and after the operation of cutting. It should be appreciated that, in FIG. 7, the inner sheet 12 and the waist region elastic sheets 14 are not illustrated in order to clarify a positional relation between the opening 15 and the leg elastics' front and rear halves 29, 30.

In FIG. 7 (a), the line along which the web of sheet defining the chassis 31 will be cut by the cutter 39 is indicated by the broken line 15a. As will be apparent from FIG. 7 (a), the web of sheet defining the chassis 31 is cut together with the continuous leg elastics' front and rear halves 29, 30 in the distance reducing segment 34. After the web of sheet defining the chassis 31 has been cut together with the continuous leg elastics' front and rear halves 29, 30 as indicated by the broken line 15a, the cut area is opened right and left as illustrated by FIG. 7 (b) under contractile force of the continuous leg elastics' front and rear halves 29, 30 and thereby the opening 15 is formed.

In a fifth step, the liquid-absorbent panel 16 is joined to the web of sheet defining the chassis 31 to cover the opening 15. The liquid-absorbent panels 16 are fed in the direction of the arrow A by a fourth roller 40 in the form of liquid-absorbent web 42 which is continuous in a longitudinal direction of the individual liquid-absorbent panels 16. The liquid-absorbent web 42 is cut by a cutter 41 operatively associated with the fourth roller 40 and the front and rear ends 19, 20 are defined. In this manner, the individual liquid-absorbent panels 16 are obtained. It should be noted here that, if the individual liquid-absorbent panels 16 are fed to the web of sheet defining the chassis 31 without appropriate redirection after cutting, the individual liquid-absorbent panels 16 will be out of phase by an angle of about 90° relative to the openings 15 extending orthogonally to the upper and lower ends 35, 36 and, in consequence, the liquid-absorbent panels 16 will be unable to cover the openings 15 completely. To overcome this problem, the fourth roller 40 is provided with the function to rotate the liquid-absorbent panels 16 by an angle of about 90° so that the liquid-absorbent panels 16 may be fed in phase with the opening 15.

The liquid-absorbent panel 16 fed onto the web of sheet defining the chassis 31 in this manner has its surface opposed to its surface provided with the leak-barrier cuffs 21 joined to the web of the inner sheet 12 constituting the web of the chassis defining sheet 31. In this step, the liquid-absorbent panel 16 is bonded to the web of the inner sheet 12 by adhesive (not shown).

In a sixth step, the leg side edges 25 are formed between each pair of the adjacent liquid-absorbent panels 16 arranged at regular intervals. Specifically, a circular opening extending through the web of sheet defining the chassis 31 in the thickness direction is formed between each pair of the adjacent liquid-absorbent panels 16 to define the leg side edges 25.

In a seventh step, the web of sheet defining the chassis 31 formed with the leg side edges 25 is folded into the shape of the diaper. More specifically, the web of sheet defining the chassis 31 is folded along the center line bisecting a dimension between the upper and lower ends 35, 36 and the web of sheet defining the chassis 31 folded in this state is cut off in regular cycles at positions indicated by the imaginary cutting lines 43 in FIG. 5. The imaginary cutting line 43 corresponds to the position of the cycle t in FIG. 6, i.e., corresponds to the middle of the circular leg side edge 25 as viewed in the conveying direction. By cutting off the web of sheet defining the chassis 31 and joining the cut off edges to each other, the assembly is shaped in the diaper of FIG. 1. The cut off edges as have been described above define the side edges 17, 18 of the chassis 2 and the upper and lower ends 35, 36 placed one upon another define the waist-opening 10. The center line R-R corresponds to the center line Q-Q after the web of the chassis defining sheet 31 has been cut off and therefore these two center lines are substantially identical to each other.

The diaper 1 is formed by the method comprising a series of steps as has been described above and such method allows the diapers to be made at a high speed and a row cost.

In the diaper 1 as has been described above, with the leg elastics' front and rear halves 29, 30 as well as the waist region elastic sheets 14 being kept in stretched state, the opening 15 is formed so that the opening 15 may be pulled outward in the transverse direction X under contractile force of the leg elastics' front and rear halves 29, 30 and the waist region elastic sheets 14. As a result, the opening space of the opening 15 enlarged in the transverse direction X. The liquid-absorbent panel 1 is attached to the chassis to cover the opening 15 having its opening space enlarged in this manner. After the liquid-absorbent panel 16 has been attached, the leg elastics' front and rear halves 29, 30 and the waist region elastic sheets 14 are left contract. In the crotch region 6, the leg elastics' front and rear halves 29, 30 are interrupted by the opening 15 and therefore the contractile force thereof is not exerted on the liquid-absorbent panel 16. The waist region elastic sheets 14 also are partially interrupted by the opening 15 in the crotch region 6 and the contractile force exerted on the liquid-absorbent panel 16 is correspondingly reduced. In this way, the liquid-absorbent panel 16 is not contracted in the transverse direction X and the opening space of the opening 15 can be maintained.

In the crotch region, the leg elastics' front and rear halves 29, 30 are attached under tension in the transverse direction X and then cut off. Consequently, in the areas of the crotch region 6 in which the leg elastics' front and rear halves 29, 30 have been attached, the contractile force effectively pulls the opening 15 in the transverse direction X.

In such diaper 1, a width dimension of the crotch region 6 after the opening 15 has been formed is larger than that before the opening 15 is in the form of the cut-in or before pulled in the transverse direction X. Correspondingly, the leg side edges 25 can be formed deeper toward the longitudinal center line P-P to broaden the opening 11. Specifically, the dimension of the crotch region 6 in the transverse direction X is larger than the waist-opening 10, i.e., the diaper 1 has a shape spreading out in a fan-like form. By dimensioning the leg-opening in this manner, it is possible to prevent the wearer's legs from being caught by the diaper 1 and thereby the diaper 1 can be smoothly put on the wearer's body.

It is possible to enlarge the size of the leg-opening 11 merely by forming the opening 15 and therefore it is unnecessary to lengthen the cycle t in the conveying direction in accordance with the leg-opening. In this way, the cost can be correspondingly reduced. Furthermore, the waist-opening 10 would not become uneconomically larger since it is unnecessary to lengthen the cycle t and, in consequence, it is possible to prevent the front and rear waist regions 4, 5 from getting wrinkles due to the economically enlarged waist-opening 10. By preventing the front and rear waist regions 4, 5 from getting wrinkles, it is possible to minimize the gap possibly left between the diaper and the wearer's body and thereby to keep the front and rear waist regions 4, 5 in close contact with the wearer's body. Thereby leakage of bodily fluids such as urine beyond the waist opening 10 can be prevented. Furthermore, it is also possible to prevent compression marks due to the wrinkles from being left on the wearer' skin by preventing the front and rear waist regions 4, 5 from getting wrinkles.

In the course of forming the opening 15, the inner and outer sheets 12, 13 are cut together with the leg elastics' front and rear halves 29, 30 so that contractile force of these elastics 29, 30 do not act on the liquid-absorbent panel 16. Consequentially, it is possible to prevent the liquid-absorbent panel 16 from getting wrinkles due to contractile force of these elastics 29, 30. Without wrinkles, the liquid-absorbent panel 16 can be kept in close contact with the wearer's crotch and thereby bodily fluids such as urine can be directly absorbed by the liquid-absorbent panel 16 to assure that bodily fluids such as urine can be further reliably prevented.

The opening 15 occupies the respective portions of the waist region elastic sheets 14 adjacent the crotch region 6 so that the opening 15 may be pulled in the transverse direction X also in the front and rear waist regions 4, 5 to broaden the dimension of the diaper in the transverse direction in the vicinity of the crotch region 6 and simultaneously to prevent the liquid-absorbent panel 16 from getting wrinkles. In the vicinity of the waist-opening 10, the waist region elastic sheets 14 are not occupied by the opening 15 and effectively act on the waist regions 4, 5. As a result, the diaper takes the shape broadened toward the crotch region 6 so that the front and rear waist regions 4, 6 may be kept in close contact with the wearer's skin and leakage of bodily fluids such as urine beyond the waist-opening 10 may be reliably prevented.

The liquid-absorbent panel 16 is attached to the chassis 2 to cover the opening 15 so that the garment-facing side of the liquid-absorbent panel 16 can be visually recognized through the outer sheet 13 of the chassis 2. When the garment-facing outer surface of the liquid-absorbent panel 16 is provided with graphics or logos, these graphics or logos will be directly visible through the opening 15.

In the present embodiment, a leak-barrier film may be sandwiched between the liquid-absorbent panel 16 and the inner sheet 12 to improve a leak-barrier property. It is also possible to attach the leak-barrier film to the outer sheet 13 after the liquid-absorbent panel 16 has been attached to the chassis 2.

While the liquid-absorbent panel 16 is attached to the side of the inner sheet 12, i.e., to the skin-facing inner surface in the present embodiment, it is possible to attach the liquid-absorbent panel 16 to the side of the outer sheet 13, i.e., to the garment-facing outer surface. When the liquid-absorbent panel 16 is attached to the garment-facing outer surface, irregularities facing the wearer's skin may be reduced and thereby irritation to the wearer's skin may be alleviated. In addition, the liquid-absorbent panel 16 provided with graphics or logos, if it is applied, such graphics or logos will be directly visible n a wider range.

In the step of forming the opening 15, the web of sheet defining the chassis 31 may be formed with a slit vertically extending between the upper and lower ends 35, 36 or cut off a portion of the web of chassis defining sheet 13 having a certain width in the conveying direction to an oval opening. While the opening 15 extends across the crotch region 6 into respective parts of the front and rear waist regions 4, 5 in the illustrated embodiment, the opening 15 may extend at least across the crotch region 6. It is also possible to form a plurality of the openings 15, for example, an opening extending across the front waist region into a part of the crotch region 6 and an opening extending across the rear waist region 5 into a part of the crotch region 6. When these two openings are formed, one of them is aligned with the wearer's anus and the other is aligned with the wearer's external genital organ so that these two openings may serve as a let-through passage for feces and as a let-through passage for urine, respectively.

While the rubber thread or rubber ribbon is used for the leg elastics' front and rear halves 29, 30 in the illustrated embodiment, it is possible to use elastic sheets for the same purpose. The elastic members used in the present embodiment are more advantageous than the elastic sheets in view of manufacturing cost. Use of the elastic sheets is advantageous in that contractile force can be evenly exerted on the opening 15 over a wide range and thereby irregularities of the periphery of the opening 15 can be alleviated.

While the leg elastics' front and rear halves 29, 30 are attached so that the distance increasing segment 33 and the distance reducing segment 34 are contiguously alternate, the present invention is not limited to such arrangement so far as the continuous elastics may be interrupted in the crotch region 6. In other words, it is essential that the opening 15 may be pulled in the transverse direction X under contractile force of the elastics.

While the waist region elastic sheets 14 are used as the waist region elastics in the present embodiment, it is possible to use rubber thread or rubber ribbon also may be used.

The invention claimed is:

1. A wearing article, comprising:
   a chassis having
      a longitudinal direction, a transverse direction perpendicular to the longitudinal direction,
      a skin-facing inner surface, a garment-facing outer surface opposite to the skin-facing inner surface,
      a front waist region, a rear waist region and a crotch region extending between said front and rear waist regions, said regions being contiguous one with another,
      a liquid-absorbent structure lying at least in said crotch region, waist region elastics attached under tension in said transverse direction to said front and rear waist regions, respectively, and leg elastics attached under tension to said chassis, wherein said chassis is contoured by front and rear ends opposed to each other in said longitudinal direction and extending in said transverse direction and side edges opposed to each other in said transverse direction and extending in said longitudinal direction so that said front and rear ends cooperate with each other to form a waist-opening and said side edges cooperate with each other to form a pair of leg-openings in said crotch region, said chassis further includes an opening formed to extend from at least one of said front and rear waist regions across said crotch region, and said liquid-absorbent structure is attached to said chassis to cover said opening, said opening is deformable under contraction of said waist region elastics in said transverse direction, said waist region elastics are waist region elastic sheets and each of which is directly sandwiched between the skin-facing inner surface of the chassis and the liquid-absorbent structure, partial sections of the opening in the front and rear waist regions are formed in the respective waist region elastic sheets, and the leg elastics extending along said side edges of the crotch region intersect the opening in the crotch region.

2. The wearing article defined by claim 1, wherein said side edges of said chassis comprise side edges of the front and rear waist regions lying in said front and rear waist regions, and side edges of the crotch region lying in said crotch region.

3. The wearing article defined by claim 2, wherein at least parts of respective said leg elastics lie outboard of said opening as viewed in said transverse direction.

4. The wearing article defined by claim 3, wherein the liquid-absorbent structure overlaps the leg elastics in the crotch region of the chassis.

5. The wearing article defined by claim 1, wherein the liquid-absorbent structure covers the opening entirely and extends beyond a circumferential edge of the opening.

6. The wearing article defined by claim 5, wherein the liquid-absorbent structure comprises a pair of barriers opposite to each other in the transverse direction, and each of the barriers includes a fixed side edge directly fixed to the waist region elastic sheets.

7. The wearing article defined by claim 6, wherein each of the fixed side edges of the barrier is between the corresponding side edge of the crotch region and the circumferential edge of the opening in the transverse direction.

8. The wearing article defined by claim 6, wherein each of the barrier further comprises a free side edge opposite to the fixed side edge in the transverse direction, and in the crotch region, a segment of the circumferential edge of the opening is arranged between the fixed side edge and the free side edge in the transverse direction.

* * * * *